United States Patent
Jaeb

(10) Patent No.: US 8,075,503 B2
(45) Date of Patent: Dec. 13, 2011

(54) SYSTEM AND METHOD FOR TREATING A WOUND USING ULTRASONIC DEBRIDEMENT

(75) Inventor: Jonathan P. Jaeb, Boerne, TX (US)

(73) Assignee: KCI Licensing, Inc., San Antonio, TX (US)

(*) Notice: Subject to any disclaimer, the term of this patent is extended or adjusted under 35 U.S.C. 154(b) by 707 days.

(21) Appl. No.: 11/656,630

(22) Filed: Jan. 23, 2007

(65) Prior Publication Data
US 2007/0239078 A1    Oct. 11, 2007

Related U.S. Application Data

(60) Provisional application No. 60/761,289, filed on Jan. 23, 2006.

(51) Int. Cl.
*A61M 35/00* (2006.01)

(52) U.S. Cl. ......... 601/2; 601/3; 600/439; 604/505; 604/22

(58) Field of Classification Search ......... 601/2–3; 600/439; 604/505, 22
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,040,414 A | 8/1977 | Suroff |

(Continued)

FOREIGN PATENT DOCUMENTS

AU    550575 A1    8/1982

(Continued)

OTHER PUBLICATIONS

N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96 (certified translation).

(Continued)

*Primary Examiner* — Brian Casler
*Assistant Examiner* — Rajeev Siripurapu
(74) *Attorney, Agent, or Firm* — SNR Denton US LLP

(57) ABSTRACT

A wound treatment system includes a distribution manifold, a reduced pressure source, a fluid delivery source, and an ultrasonic energy transducer. Reduced pressure and fluid delivery may be applied to the wound through the distribution manifold. The ultrasonic energy transducer is configured to deliver ultrasonic energy to the wound to debride the wound. The ultrasonic energy transducer may be either a piezoelectric transducer or a surface acoustic wave device. The ultrasonic energy transducer may be placed adjacent to the distribution manifold to deliver ultrasonic energy directly to the wound or may be coupled to an acoustically-conducting membrane positioned between the distribution manifold and the wound.

5 Claims, 1 Drawing Sheet

U.S. PATENT DOCUMENTS

| | | | |
|---|---|---|---|
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielson | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,982,730 A | 1/1991 | Lewis, Jr. | |
| 4,985,019 A | 1/1991 | Michelson | |
| 5,016,615 A * | 5/1991 | Driller et al. | 601/2 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,312,329 A | 5/1994 | Beaty et al. | |
| 5,342,376 A | 8/1994 | Ruff | |
| 5,344,415 A | 9/1994 | DeBusk et al. | |
| 5,358,494 A | 10/1994 | Svedman | |
| 5,391,144 A | 2/1995 | Sakurai et al. | |
| 5,437,622 A | 8/1995 | Carion | |
| 5,437,651 A | 8/1995 | Todd et al. | |
| 5,524,624 A | 6/1996 | Tepper et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,626,554 A | 5/1997 | Ryaby et al. | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,142,982 A | 11/2000 | Hunt et al. | |
| 6,171,265 B1 | 1/2001 | Novak et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,916,296 B2 | 7/2005 | Soring et al. | |
| 7,128,719 B2 * | 10/2006 | Rosenberg | 601/2 |
| 7,410,469 B1 * | 8/2008 | Talish et al. | 601/2 |
| 7,500,956 B1 * | 3/2009 | Wilk | 601/2 |
| 7,569,742 B2 | 8/2009 | Haggstrom | |
| 2002/0055693 A1 * | 5/2002 | Thompson et al. | 601/2 |
| 2002/0077661 A1 | 6/2002 | Saadat | |
| 2002/0115951 A1 | 8/2002 | Norstrem et al. | |
| 2002/0115952 A1 * | 8/2002 | Johnson et al. | 602/41 |
| 2002/0120185 A1 | 8/2002 | Johnson | |
| 2002/0143286 A1 | 10/2002 | Tumey | |
| 2002/0156400 A1 | 10/2002 | Babaev | |
| 2003/0040687 A1 | 2/2003 | Boynton et al. | |
| 2003/0212351 A1 * | 11/2003 | Hissong et al. | 601/2 |
| 2004/0030304 A1 | 2/2004 | Hunt et al. | |
| 2004/0077977 A1 | 4/2004 | Ella et al. | |
| 2005/0020966 A1 | 1/2005 | Soring et al. | |
| 2006/0241533 A1 * | 10/2006 | Geller | 601/4 |
| 2009/0264807 A1 | 10/2009 | Haggstrom | |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 43 06 478 A1 | 9/1994 |
| DE | 29504378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1 219 278 A2 | 7/2002 |
| EP | 1018967 B1 | 8/2004 |
| GB | 692578 | 6/1953 |
| GB | 1574066 | 9/1980 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| JP | 2003-515424 | 5/2003 |
| RU | 2112571 C1 | 6/1998 |
| RU | 2175539 C2 | 11/2001 |
| RU | 2261692 C2 | 10/2005 |
| SG | 71559 | 4/2002 |
| SU | 587941 A1 | 1/1978 |
| SU | 1461466 A1 | 2/1989 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/17933 | 5/1997 |
| WO | WO 97/18007 | 5/1997 |
| WO | WO 99/13793 | 3/1999 |

OTHER PUBLICATIONS

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

King, W. W. K. et al.: "Debridement of Burn Wounds with a Surgical Ultrasonic Aspirator", Burns, vol. 22, No. 4, 1996, pp. 307-309.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Vanderburgh, E. et al.: "Debridement of Vaginal Radiation Ulcers Using the Surgical Ultrasonic Aspirator", Gynecologic Oncology, vol. 39, 1990, pp. 103-104.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Uhlemann, C. et al.: "Therapeutic Ultrasound in Lower Extremity Wound Management", International Journal of Lower Extremity Wounds, 2(3), 2003, pp. 152-157.

Herte, Mary C., M.D. et al.: "Comparative Wound Healing in Animal Subjects Using the CUSA™ System vs. Conventional Surgical Instruments"; Release at the American Society of Plastic and Reconstructive Surgeons, Nov. 1978, pp. 19.

Chariker, Mark E., M.D., et al: "Effective Management of Incisional and Cutaneous Fistulae with Closed Suction Wound Drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N. a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

Kosaka, Masaaki et al. "'Pocket Measure': An Exclusive Tool for Measuring and Recording Pressure Ulcer Pockets"; Journal of Plastic and Reconstructive Surgery, vol. 114, No. 2, Aug. 2004 (pp. 624-625) (2 pages).

* cited by examiner

SYSTEM AND METHOD FOR TREATING A WOUND USING ULTRASONIC DEBRIDEMENT

CROSS REFERENCE TO RELATED APPLICATIONS

This application claims the benefit of U.S. Provisional Application No. 60/761,289, filed Jan. 23, 2006, which is hereby incorporated by reference.

BACKGROUND OF THE INVENTION

A. Field of the Invention

The invention relates generally to wound treatment systems and methods, and more specifically to a system and method of treating a wound by combining ultrasonic debridement and reduced pressure therapy.

B. Description of Related Art

Wounds to the skin typically fall into two categories: chronic and acute. The natural healing mechanism in animals repairs acute wounds quickly by closing the wound, filling in lost tissue, and covering the wound with a new layer of skin. Those having observed wound healing in children often observe the healing of small acute wounds in a few days. Chronic wounds are often wounds in which the natural healing mechanisms have been impaired. Chronic wounds typically linger for extended periods of time and may never heal. Such wounds are often observed among the elderly or people suffering from diabetes. Another problem associated with wounds is infection. Infection is the invasion of a wound by pathogenic microorganisms or bacteria that grow within the wound, produce toxins, and subsequently injure the tissue surrounding the wound. To reduce the chance for infection of a wound, the wound is first cleaned to remove those microorganisms or bacteria that may have invaded the wound when it was created. Next, the wound typically is debrided or sterilized to remove nonviable or necrotic tissue and any microorganisms or bacteria resident within the wound. The third step in the treatment of a wound is to apply a dressing to cover the wound and promote its healing with the application of medication.

The debriding of a wound is often accomplished with mechanical surgical methods, referred to as sharps debridement. Specifically, the non-viable or necrotic tissue is cut from the wound and removed. Sometimes, surgical treatment of a wound will trigger the body's response to an acute wound and the wound will heal.

While the debridement process often involves cutting away tissue within the wound, recent efforts have involved the use of ultrasonic energy. A description of the use of ultrasonic energy and its use on skin appears in the following U.S. patents: Suroff, U.S. Pat. No. 4,040,414 (Ultrasonic Personal Care Instrument and Method); Beaty, et al., U.S. Pat. No. 5,312,329 (Piezo Ultrasonic and Electrosurgical Handpiece); Sakurai, et al., U.S. Pat. No. 5,391,144 (Ultrasonic Treatment Apparatus); Novak, et al., U.S. Pat. No. 6,171,265 (Handpiece for Use With a Multifunctional Operating Endoscopic Instrument); and in the following published PCT application: Babaev, WO 97/17933 (Method of Spraying A Surface Using Ultrasonic Radiation). Further descriptions are found in the following articles: King, et al., Burns, Vol. 22, No. 4, Pg. 307, (Debridement of Burn Wounds with a Surgical Ultrasonic Aspirator); Vanderburgh, et al., Gynecologic Oncology, Vol. 39, Pg. 103 (1990); (Debridement of Vaginal Radiation Ulcers Using the Surgical Ultrasonic Aspirator); and Herte, et al., Am. Society of Plastic and Reproductive Surgeons Prelim. Rpt. (November 1978); (Comparative Wound Healing in Animal Subjects Using the Cavitron Ultrasonic Surgical Aspirator vs. Conventional Surgical Instrument).

Further, in recently issued U.S. Pat. No. 6,916,296 to Soring, et al., entitled System for Antiseptic Surgery, a system using ultrasound was proposed for wound healing. Specifically, a device called a sonotrode is placed in a liquid within the wound. The sonotrode generates ultrasonic vibrations and cavitations in the liquid that leads to destruction of the bacteria cells. Specifically, the high level of energy released in the fluid kills the bacteria cells by rupturing their cell walls. While U.S. Pat. No. 6,916,296 reports a significant reduction in germ count in a wound, it is also taught that high levels of energy can be used for very short periods of time, or that lower levels of energy can be used for longer periods of time—up to several minutes.

In practice, the use of ultrasound to debride wounds involves relatively high amounts of ultrasonic energy typically applied in a focused manner to energize a relatively small area of a wound for a short period of time. The area over which ultrasonic energy is broadcast at any given time is typically less than about 5 $cm^2$. Since the treatment is focused, the ultrasonic energy is typically only applied for less than about 60 seconds to any specific area.

Following debridement, wounds are dressed to cover the wound and promote healing. In recent years, it has been found that the application of reduced pressure to a wound promotes healing in many cases. This is particularly evident in chronic wounds, such as those that develop in elderly patients, but may also occur in any type of wound. Studies have also revealed that frequent irrigation of a wound helps promote healing by aiding in the removal of wound exudate, unwanted bioburden, and optionally, serving as an effective vehicle for the application & delivery of medication. Examples of wound treatment systems employing some of these techniques are found in the following U.S. patents: Zamierowski, U.S. Pat. No. 4,969,880 (Wound Dressing and Treatment Method); Zamierowski, U.S. Pat. No. 5,100,396 (Fluidic Connection System and Method); Zamierowski, U.S. Pat. No. 5,261,893 (Fastening System and Method); Zamierowski, U.S. Pat. No. 5,527,293 (Fastening System and Method); Argenta, et al., U.S. Pat. No. 5,636,643 (Wound Treatment Employing Reduced Pressure); Argenta, et al., U.S. Pat. No. 5,645,081 (Method of treating tissue damage and apparatus for same); Zamierowski, U.S. Pat. No. 6,071,267 (Medical Patient Fluid Management Interface System and Method); Vogel, et al., U.S. Pat. No. 6,135,116 (Method for Treating Ulcers); and Hunt, et al., U.S. Pat. No. 6,142,982 (Portable wound treatment apparatus).

While ultrasonic debridement has been taught as a way of initially clearing a wound of nonviable or necrotic tissue, the procedure has not gained acceptance as part of broad-based system for accelerating healing of a wound, in part due to the labor-intensive process involved with traditional ultrasonic debridement. A need currently exists for a system that utilizes ultrasonic energy at low energy levels over a prolonged period of time to debride a wound. For ease of use and improvement in performance, the application area over which the ultrasonic energy is applied should be relative large compared to existing procedures, which call for a more focused beam. Also needed is a system that employs a non-focused, low energy debridement procedure such as ultrasound, with reduced pressure therapy, and optionally, with a system providing fluid irrigation and removal of debrided tissue.

All of the patents, patent applications, and other publications referenced herein are incorporated by reference to the maximum extent allowable by law.

SUMMARY OF THE INVENTION

The problems presented by wound treatment systems tissue dressings are solved by the systems and methods of the present invention. In accordance with one embodiment of the present invention, a wound treatment system is provided that includes a distribution manifold, a reduced pressure source, and an ultrasonic energy transducer. The reduced pressure source is fluidly connected to the distribution manifold to deliver reduced pressure to a tissue site, and the ultrasonic energy transducer is positioned adjacent to the distribution manifold.

In accordance with another embodiment of the present invention, a wound treatment system for debriding and healing a wound site includes a distribution manifold, a reduced pressure source fluidly connected to the distribution manifold, an acoustically-conducting membrane, and an ultrasonic energy transducer. The acoustically-conducting membrane is positioned between the distribution manifold and the wound site, and the ultrasonic energy transducer is coupled to the membrane.

In still another embodiment of the present invention, a wound treatment system includes means for dressing a wound, means for reducing pressure at the wound, and means for debriding the wound.

In accordance with yet another embodiment of the present invention, an ultrasonic wound treatment system for treating a wound site includes an ultrasonic energy transducer configured to deliver ultrasonic energy to substantially all of the wound site at a power level less than about 1 W/cm$^2$. The ultrasonic energy is delivered during a selected duration such that substantially all of the wound site is exposed to ultrasonic energy for at least ten minutes per day (10 min/day).

In yet another embodiment of the present invention, a wound treatment system includes a distribution manifold configured to be placed in fluid communication with a wound. A fluid source is fluidly connected to the distribution manifold and configured to deliver a fluid to the wound during a first selected duration. An ultrasonic energy transducer is configured to be placed in ultrasonic communication with and deliver ultrasonic energy to the wound during a second selected duration. A reduced pressure source is fluidly connected to the distribution manifold and configured to deliver a reduced pressure to the wound during a third selected duration.

In accordance with another embodiment of the present invention, a method for treating a wound includes simultaneously applying reduced pressure and ultrasonic energy to the wound to debride and heal the wound.

In still another embodiment of the present invention, a method for treating a wound includes delivering a fluid to the wound and allowing the fluid to dwell at the wound for a selected duration. Ultrasonic energy is applied to the wound during the selected duration, and a reduced pressure is applied to the wound following the selected duration to remove the fluid and any debrided tissue.

In another embodiment of the present invention, a multipurpose wound dressing includes a distribution manifold that is configured to distribute a reduced pressure to a wound site. An ultrasonic energy transducer is positioned adjacent to the distribution manifold to provide ultrasonic debridement to the wound site.

In yet another embodiment of the present invention, a multipurpose wound dressing includes a distribution manifold configured to distribute a reduced pressure to a wound site. An acoustically-conducting membrane is positioned on a tissue contact side of the distribution manifold and is configured to contact the wound site. An ultrasonic energy transducer is operatively coupled to the acoustically-conducting membrane.

Other objects, features, and advantages of the present invention will become apparent with reference to the drawings and detailed description that follow.

DETAILED DESCRIPTION OF A PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
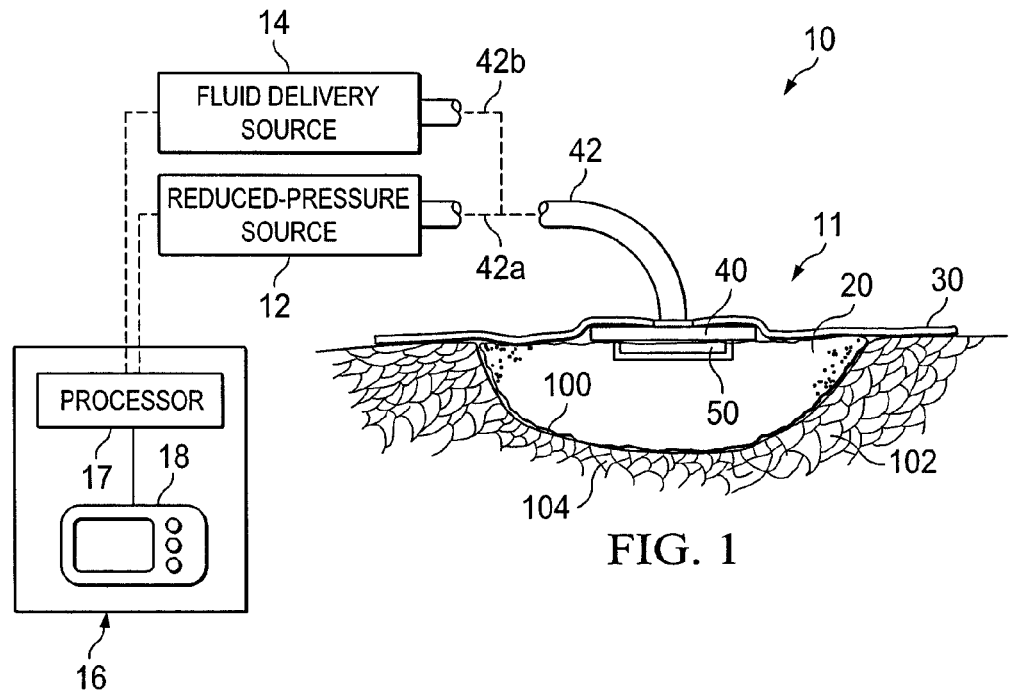
FIG. 1 illustrates a front cross-sectional view of a system for applying reduced pressure and ultrasonic energy to a wound or tissue site according to an embodiment of the present invention.
Figure 2:
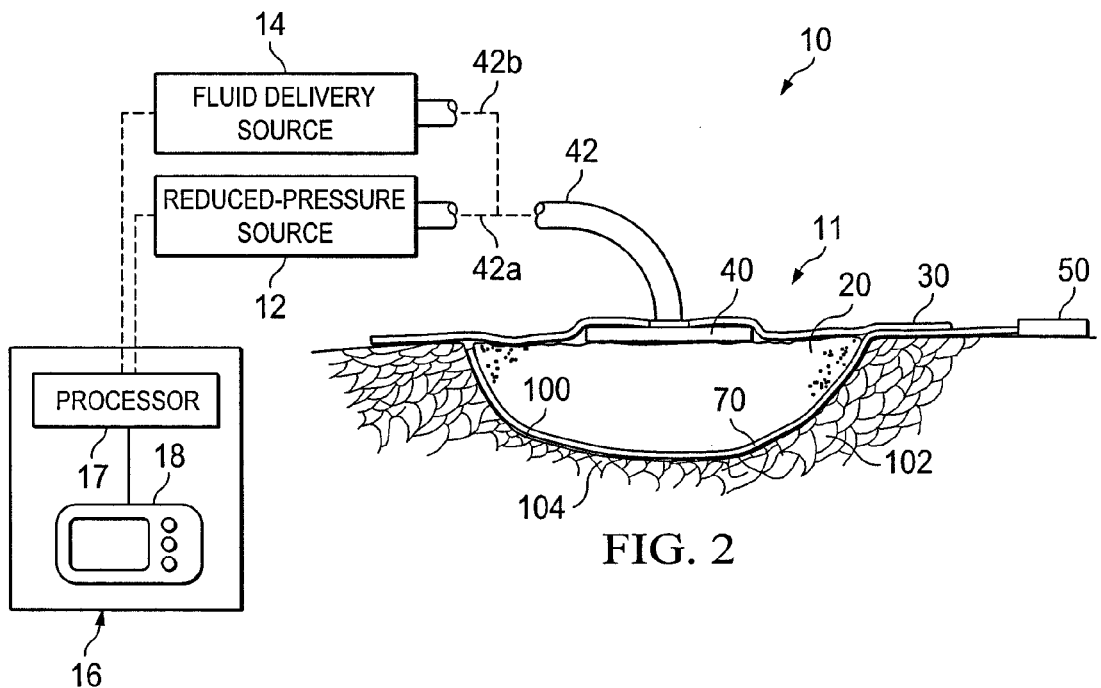
FIG. 2 depicts a front cross-sectional view of a system for applying reduced pressure and ultrasonic energy to a wound or tissue site according to an embodiment of the present invention.

Referring to FIGS. 1 and 2 a wound treatment system 10 according to an embodiment of the present invention includes a multipurpose wound dressing 11 having the capability of providing ultrasonic debridement to the wound, a reduced pressure source 12 to deliver reduced or subatmospheric pressure to the wound, and optionally, a fluid delivery source 14 to irrigate the wound with a fluid. A computer system 16 including a processor 17 and a user interface 18 may be provided to control all of the system functions of the reduced pressure therapy, debridement, and fluid delivery.

Referring more specifically to FIG. 1, the wound treatment system 10 is preferably used to debride and promote the healing of a wound site 100. Wound site 100 is surrounded by tissue 102. At least a portion of the wound site 100 includes a compromised layer of tissue 104, which may include a mixture of healthy, and non-viable live cells, dead cells, and varying amounts of contaminants such as micro-organisms and bacteria. Experimentation has revealed that this compromised layer of tissue may be as thick as 5 mm. While conventional treatment of the surface of the wound may remove dead tissue and bacteria on the surface of the wound, the bacteria beneath the surface are not removed and may continue to harbor infections. Debridement of the wound assists in the removal of this hidden bacteria.

The multipurpose wound dressing 11 includes a distribution manifold 20, an ultrasonic energy transducer 50, a tube 42 for fluidly communicating with the distribution manifold, and, optionally, a drape 30. The distribution manifold 20 is configured to be placed adjacent to the wound site 100. The distribution manifold 20 includes a plurality of flow channels or pathways to facilitate the distribution of reduced pressure or fluids to or from the wound site. In one embodiment the distribution manifold 20 is a porous foam and includes a plurality of interconnected cells or pores that act as flow channels. The porous foam may be a polyurethane, open-cell, reticulated foam such as GranuFoam manufactured by Kinetic Concepts, Inc. of San Antonio, Tex. If an open-cell foam is used, the porosity may vary, but is preferably about 400 to 600 microns.

The drape 30 is positioned over the distribution manifold 20 when an open wound site is treated to seal and isolate the wound site. If the wound site being treated is a subcutaneous or deep tissue wound site, drape 30 may not be necessary to maintain reduced pressure at the wound site. Drape 30 may be any biocompatible, flexible material. Drape 30 may be impermeable or semi-permeable to liquid, gas, or both depending upon a given application. A reduced pressure applicator 40 is placed under the drape 30 and over the distribution manifold 20. The tube 42 is fluidly connected at a distal end to the applicator 40 and is fluidly connected at a proximal end to the reduced pressure source 12, which may be a pump or a wall suction outlet. Near the reduced pressure source 12, the tube 42 is schematically represented as reduced pressure delivery tube 42a. The reduced pressure source is capable of supplying reduced pressure to the wound through the reduced pressure delivery tube 42a and distribution manifold 20. While the applicator 40 provides one means of transferring reduced pressure from the reduced pressure delivery tube 42a to distribution manifold 20, applicator 40 may be omitted if the reduced pressure delivery tube 42a is placed in direct fluid communication with distribution manifold 20.

A fluid delivery tube 42b may be provided to deliver a fluid to the wound and may similarly be fluidly connected to the distribution manifold by the applicator 40. The representation of tubes 42, 42a, and 42b in FIGS. 1 and 2 illustrate that a common applicator may be used for delivering reduced pressure and fluids to the distribution manifold 20. This may be accomplished by using the tube 42 for only one purpose at any time. More specifically, the tube 42 may be used to alternately deliver reduced pressure and fluids. In another embodiment, the tube 42 may be a dual lumen tube having a lumen for reduced pressure delivery and a lumen for fluid delivery. In still another embodiment (not illustrated), separate tubes may be used to fluidly communicate with the distribution manifold 20. If separate tubes are used, the use of an applicator 40 is optional.

The ultrasonic energy transducer 50 may include a frequency generator and an amplifier and is used to transmit ultrasonic energy to the wound site 100. The ultrasonic energy transducer may be a piezoelectric transducer or a surface wave acoustic device. In FIG. 1, the ultrasonic energy transducer 50 is placed between the applicator 40 and distribution manifold 20 to emit a low level of ultrasonic energy. The ultrasonic energy transducer 50 may be connected to one or both of the applicator 40 and the distribution manifold 20, or alternatively may be placed between the applicator 40 and distribution manifold 20 without physical connection to either. In one embodiment, the ultrasonic energy transducer 50 may be embedded within the distribution manifold 20.

The distribution manifold 20 acts as a transmission medium to relay ultrasonic energy to the wound site 100. When a reticulated foam is used, the transmission efficiency of the foam may be enhanced by using the fluid delivery source to infuse the foam with water, aqueous and sub-aqueous solutions, or gels. The presence of fluid within the foam improves the ability of the foam to transfer the ultrasonic energy. In this regard, the distribution manifold performs both the functions of a manifold and a transmission medium for ultrasonic energy. It should further be noted that gels or other transmission enhancing substances may be placed within or on the distribution manifold 20. For example, a gel may be placed between the distribution manifold 20 and the wound site 100 prior to the transmission of ultrasonic energy through the distribution manifold 20 to enhance energy transmission.

The amount of ultrasonic energy being applied to the wound by the ultrasonic energy transducer 50 is less than that of traditional ultrasonic debridement transducers. Preferably, if a high frequency (about 800 to 4000 kHz to) transducer is used, the power applied to the transducer is about 1.0 W/cm$^2$, and more preferably about 0.5 W/cm$^2$. If a low frequency (about 20 to 120 kHz to) transducer is used, the power applied to the transducer preferably is about 0.5 W/cm$^2$, and more preferably about 0.1 W/cm$^2$.

Referring to FIG. 2, the ultrasonic energy transducer 50 may be positioned remotely from the wound site 100 and may be operatively connected to an acoustically-conducting membrane 70 positioned between the distribution manifold 20 and the wound site 100. The membrane 70 may be connected to the distribution manifold 20, or alternatively may be placed without connection between the distribution manifold 20 and wound site 100 prior to administration of reduced pressure and ultrasonic therapies. In this embodiment, the low level of ultrasonic energy produced by the ultrasonic energy transducer 50 is transmitted across the membrane 70 and radiates into the compromised tissue layer 104. The proximity of the membrane 70 to the wound site 100 in some circumstances may improve the debridement performance of the wound treatment system 10. Since the ultrasonic energy is typically produced at low power, the ultrasonic energy transducer 50 may be positioned at or near the periphery of the wound site 100. Positioning of the membrane 70 between the distribution manifold 20 and the wound site 100 should not interfere with the capability of the distribution manifold to deliver reduced pressure or fluids to the wound site 100. In this regard, the membrane 70 is preferably formed from a naturally porous material, or alternatively is manufactured to include holes, pores, projections or other structural features that promote flow within, around, or through the membrane. The membrane may be made from a metallic foil, thin sheets of Lexan®, or any other material that is capable of conducting an ultrasonic wave.

In operation, the multipurpose dressing described herein combines reduced pressure therapy, ultrasonic debridement, and optional fluid delivery for debriding, cleaning, and healing the wound site. All of these functions may be integrated into a combined system that provides for the intermittent or continuous operation of each function individually or simultaneously, without changing the dressing between functions. Since the dressing is intended to remain in place for several days between changes, the ultrasonic energy transducer is optimized to provide debridement over long time periods at low power.

In one exemplary operational example, an irrigation or medicinal fluid is delivered by the fluid delivery source 14 to the distribution manifold during a first selected duration. Preferably, the first selected duration is about five (5) minutes. During this duration, the fluid is allowed to permeate the distribution manifold 20 and irrigate the wound site 100. During a second selected duration following the first selected duration, the fluid is allowed to dwell at the wound site and ultrasonic energy is transmitted to the wound site 100 by the ultrasonic energy transducer. The ultrasonic energy debrides the wound of nonviable and necrotic tissue. Preferably, the second selected duration is about fifteen minutes (15), or about three times the first selected duration. Following the second selected duration, transmission of ultrasonic energy is ceased, and reduced pressure is applied through the distribution manifold by the reduced pressure source. The reduced pressure removes the delivered fluid from the wound and distribution manifold, as well as wound exudate and debrided tissue. The application of reduced pressure continues for a third selected duration, which is preferably about forty (40) minutes, or about three times the second selected duration. The exemplary time durations described above may vary, and each of the procedures (i.e. fluid delivery, ultrasonic debridement, and reduced pressure therapy) may be performed independently of one another, or simultaneously with one or both of the other procedures.

It should be apparent from the foregoing that an invention having significant advantages has been provided. While the invention is shown in only a few of its forms, it is not just limited but is susceptible to various changes and modifications without departing from the spirit thereof.

I claim:

1. A method for treating a wound site comprising:
   providing a wound treatment system, the wound treatment system comprising:
   a distribution manifold comprising a porous foam having a plurality of flow channels for distributing reduced pressure,
   a reduced pressure source fluidly connected to the distribution manifold to deliver reduced pressure to the wound site,
   a reduced pressure applicator fluidly coupled to the distribution manifold and the reduced pressure source,
   a drape for positioning over the distribution manifold and at least a portion of the reduced pressure applicator, and
   an ultrasonic energy transducer configured to deliver ultrasonic energy to substantially all of the wound site at a power level less than about 1 W/cm$^2$;
   disposing the porous foam of the distribution manifold adjacent to the wound site;
   fluidly coupling the reduced pressure applicator to the reduced pressure source;
   positioning the drape over the distribution manifold and at least a portion of the reduced pressure applicator;
   using the wound treatment system to debride the wound site and to provide reduced pressure therapy to the wound site without a dressing change, wherein the distribution manifold acts as a transmission medium to relay ultrasonic energy to the wound site and to transmit reduced pressure to the wound site; and
   wherein the step of using the wound treatment system to debride the wound site and to provide reduced pressure therapy to the wound site comprises:
      activating the ultrasonic energy transducer for a selective duration of at least fifteen (15) minutes whereby ultrasonic energy is provided to the wound site to debride the wound site, and
      activating the reduced pressure source to provide reduced pressure to the wound site for at least forty (40) minutes to provide reduced pressure therapy.

2. The method of claim 1, further comprising the step of providing an irrigation fluid to the distribution manifold for at least five minutes.

3. The method of claim 1, wherein the ultrasonic energy transducer has a frequency between about 800 and 4000 kHz and wherein the power applied at the wound site is less than about 0.5 W/cm$^2$.

4. The method of claim 1, wherein the ultrasonic energy transducer is placed between the distribution manifold and the reduced pressure applicator.

5. The method of claim 1, wherein the ultrasonic energy transducer is embedded in the distribution manifold.

* * * * *